(12) United States Patent
Barfoot et al.

(10) Patent No.: US 9,835,478 B2
(45) Date of Patent: Dec. 5, 2017

(54) OPTICAL POWER LIMITING METHOD USING STIMULATED BRILLOUIN SCATTERING IN FIBER OPTIC WAVEGUIDES

(71) Applicant: Halliburton Energy Services, Inc., Houston, TX (US)

(72) Inventors: David A. Barfoot, Houston, TX (US); John Maida, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 118 days.

(21) Appl. No.: 14/911,604

(22) PCT Filed: Oct. 7, 2013

(86) PCT No.: PCT/US2013/063638
§ 371 (c)(1),
(2) Date: Feb. 11, 2016

(87) PCT Pub. No.: WO2015/053736
PCT Pub. Date: Apr. 16, 2015

(65) Prior Publication Data
US 2016/0195412 A1  Jul. 7, 2016

(51) Int. Cl.
*G01D 5/353* (2006.01)
*G01V 8/16* (2006.01)
*G01N 21/47* (2006.01)
*G02B 6/02* (2006.01)
*G02B 6/293* (2006.01)
*H01S 3/11* (2006.01)
*H01S 3/30* (2006.01)

(52) U.S. Cl.
CPC ......... *G01D 5/35364* (2013.01); *G01N 21/47* (2013.01); *G01V 8/16* (2013.01); *G02B 6/02028* (2013.01); *G02B 6/29391* (2013.01); *H01S 3/11* (2013.01); *H01S 3/302* (2013.01); *G01N 2021/4709* (2013.01); *G01N 2021/4742* (2013.01); *G01N 2201/088* (2013.01)

(58) Field of Classification Search
CPC .............. G01D 5/353; G01D 5/35348; G01D 5/35312; G01K 2011/322; G01M 1/319; H01S 3/302; H01S 3/11; G01J 3/4412
USPC ....................................... 250/227.14, 227.21
See application file for complete search history.

(56) References Cited

U.S. PATENT DOCUMENTS

| 7,504,618 B2 * | 3/2009 | Hartog .................. G01J 3/4412 250/227.14 |
| 2010/0166368 A1 | 7/2010 | Oron et al. |
| 2011/0170159 A1 | 7/2011 | Donval et al. |

FOREIGN PATENT DOCUMENTS

| JP | 3850857 B2 | 11/2006 |
| WO | 2008-020170 A2 | 2/2008 |
| WO | 2012077075 A1 | 6/2012 |

OTHER PUBLICATIONS

Pureza, P. et al., "Nonlinear properties of chalcogenide glass fibers", Journal of Optoelectroics and Advanced Materials, vol. 8, No. 6, pp. 2148-2155. Dec. 2006. See abstract: pp. 2152, 2153 and Figure 10.

* cited by examiner

Primary Examiner — Que T Le
(74) Attorney, Agent, or Firm — Gilliam IP PLLC

(57) ABSTRACT

A fiber optic sensor interrogation system with inbuilt passive power limiting capability based on stimulated Brillouin scattering that provides improved safety performance for use in explosive atmospheres.

22 Claims, 16 Drawing Sheets

OPTICAL POWER LIMITING METHOD USING STIMULATED BRILLOUIN SCATTERING IN FIBER OPTIC WAVEGUIDES

BACKGROUND

Fiber optic systems are used in many applications. One of the types of applications can be described as fiber optic sensor interrogators. In a typical fiber optic sensor interrogator, light is emitted from an interrogation unit containing a laser and other optical devices. The laser may be a continuous wave (CW) laser, it may be a pulsed laser, which may include a separate amplifier and pulse generator. Or it may be a naturally pulsed laser (for example a Nd:YAG laser) without need of separate amplification or pulsing circuitry. In addition, in a typical sensing application the interrogation system may contain an optical receiver to receive back-scattered signals from the sensor in order to make a measurement. In many applications, light that is emitted from the interrogator will reflect off of a sensor and return to the interrogator, for example a Fabry-Perot cavity, or fiber Bragg grating. Another method of sensing is to use the intrinsic backscattering of the fiber through scattering processes including Rayleigh, Brillouin, and Raman scattering. The scattering processes will provide a return signal back to the interrogator that is received at the detector to make a measurement of parameters like strain, vibration, and temperature.

An important design consideration in many fiber optic sensor interrogators is in applications in which the light from the interrogation unit passes into regions that that may contain explosive atmospheres, such as the subsurface environments of oil and gas wells.

Achieving intrinsic safety with any complex electrical device is very difficult because it requires that the available electrical energy at the device be limited below the level required for ignition. This requires that only low voltages and currents are used and that no significant energy storage can occur within the device. With a fiber optic sensor, the interrogator may be placed many tens or hundreds of meters away from the hazardous region with only the fiber optic cable and passive optical sensor being within the explosive atmosphere. For years it was thought that the energy present in fiber optic sensing systems was not high enough to cause ignition and additionally, all energy was contained inside the glass fiber, therefore it was safe to use in explosive atmospheres. However, in recent years, tests have been performed that demonstrate that in explosive atmospheres ideal for ignition, it is possible for a relatively low-power optical signal, on the order of 10 s or 100 s of milliwatts average power, to cause ignition. In the case of a broken fiber, optical power can exit the fiber and be absorbed by a small dust particle. The dust particle may absorb most of the optical power and due to its low surface area, heat can accumulate in the particle rapidly until the particle reaches a high enough temperature to cause ignition.

The optical power required for ignition depends on many factors including: core size of the fiber and beam diameter, pulse duration if pulsed light, wavelength of the light, components of the flammable gas mixture, and the presence of target particles. A number of experiments have been performed to determine a safe power threshold, below which ignition cannot occur even with the most explosive gas mixtures. A power level of 35 mW has been accepted as a safe threshold level, below which ignition due to optical radiation cannot occur.

These ignition power levels are not a concern for most fiber optic sensing systems when they are operating with normal power levels required for sensing. However, the capability exists within many of some interrogator designs to generate much higher power if a fault were to occur in the system. For example, a distributed sensing method like Distributed Temperature Sensing (DTS), Distributed Acoustic Sensing (DAS), etc. may interrogate a fiber optic sensing cable using an optical time domain reflectometry method whereby a short pulse of light, on the order of tens of nanoseconds or less, is sent into the fiber repeatedly at up to tens of kilohertz repetition rate. Typically, an electrical control circuit is used to generate the timing pulse, which is sent to an optical component that controls the timing and duration of the optical pulse. If a malfunction were to occur in this pulse generating circuit due to an electronics fault, or a fault in software/firmware that may be controlling the electronics, it will be possible for the optical pulse length to exceed the desired duration. In extreme cases, the pulse duration may grow to 10 s or 100 s or 1000 s of times the normal duration, which will have the effect of increasing the average optical power by a proportional amount and may exceed the safe optical power level for operating in explosive atmospheres. Another possible fault may occur in any optical amplification component, for example an erbium-doped fiber amplifier (EDFA). The EDFA is given a control signal to set the gain to a desired level that is normally below the maximum gain that the EDFA is capable of generating. A fault in the electronics, firmware, or software controlling the EDFA may allow the gain level to exceed the desired level, allowing optical power levels to be emitted that are much higher than desired and may exceed the safety threshold for explosive atmospheres.

Prior art methods of power regulation, for example in fiber optic telecom systems, have been to use a device to monitor the power of the transmitted light by using a circulator/coupler to redirect a small percentage of the light to an optical detector. When the power indicated by the optical detector increases beyond a threshold value, an optical switch or variable optical attenuator is adjusted to attenuate the outgoing light. An electronic control circuit is used to coordinate these components. A disadvantage of such approaches though is that they involve active devices that have their own failure modes. If any one of these three components were to fail to operate properly, the safety mechanism may fail to operate.

There is a need then to move beyond these active systems to find in fiber optic interrogator systems that are more fail safe.

DETAILED DESCRIPTION

In this description then we offer a new approach by proposing a much safer fiber sensor interrogator than the prior art approaches.

In the following detailed description, reference is made that illustrate embodiments of the present disclosure. These embodiments are described in sufficient detail to enable a person of ordinary skill in the art to practice these embodiments without undue experimentation. It should be understood, however, that the embodiments and examples described herein are given by way of illustration only, and not by way of limitation. Various substitutions, modifications, additions, and rearrangements may be made that remain potential applications of the disclosed techniques. Therefore, the description that follows is not to be taken in a limited sense, and the scope of the disclosure is defined only by the appended claims.

Figure 1:
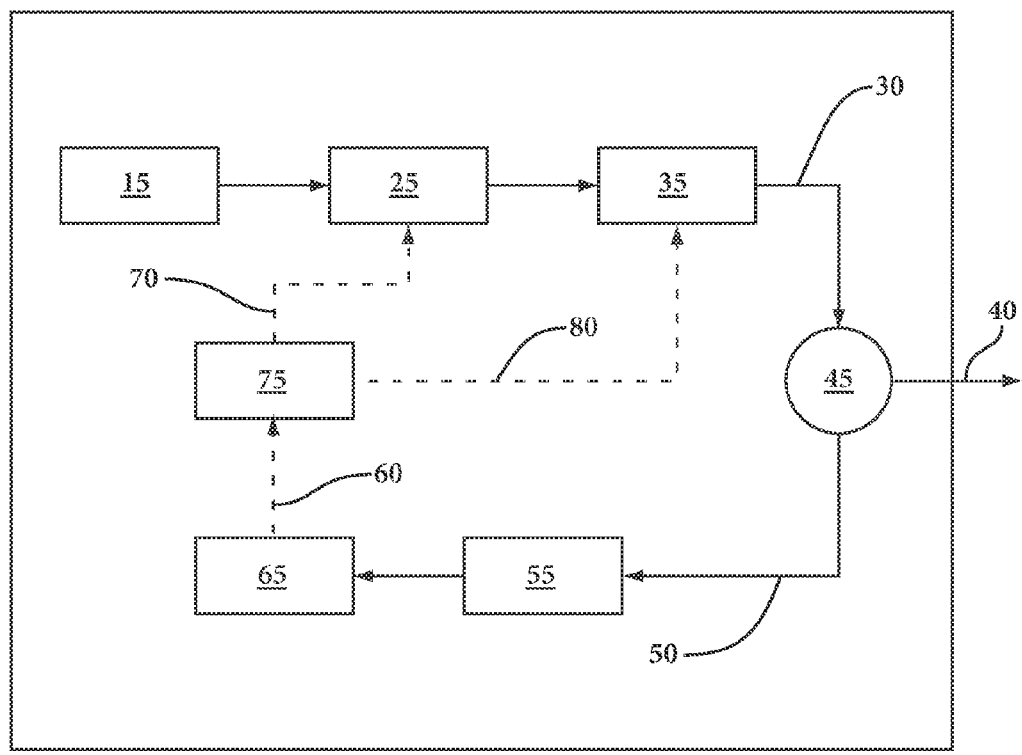
FIG. 1 illustrates a prior art high-level optical interrogator schematic.

We refer first to a high-level optical interrogator schematic provided in FIG. 1, labeled as prior art. The diagram provided in FIG. 1 is given as an example for discussion only and does not represent the properties or components of all possible fiber optic interrogator designs. The important principle to note is that such systems can be divided into a light-emitting path (upper path), and a light-receiving path (lower path). The light-emitting path performs the functions of sending the out-going or interrogating light signal into a region of interest and the light-receiving path receives an incoming or returned signal for measurement and processing. The upper path usually begins with the light source 15, often a laser. In the case of pulsed laser systems an optical amplifier 25 and an optical pulse generator 35 may follow this. The resulting pulsed light source 30 then passes to a passive optical device 45 for separating the interrogating pulsed light source light from any returning light. The outgoing light pulse source 40 then travels out into the region of interest for sensing. The returned light source, representing backscattered light signals from the region of interest also enters passive optical device 45 and is redirected 50 into the light-receiving path (lower path). Passive optical device 45 may be a coupler, a splitter, or a non-reciprocal optical device like a circulator or wavelength division multiplexer (WDM). It will be referred to in this disclosure as a circulator/coupler. It should be noted that optical amplifier 25, pulse generator 35, and laser 15 may be separate components, or combined into a single component with the amplifier and pulser being optional. Additional optical amplifiers, switches, filters, etc., may also be present in the light emitting path and may require control signals in order to operate properly.

Turning now to the light-receiving path (lower path) the returned back-scattered signals 50 from the region of interest are fed to an optical receiver/detector 55 that may contain photo-detectors as well as hardware and/or software needed to detect and analyze the returned signals. The analog signals from receiver/detector 55 may then pass to an analog-to-digital (ADC) converter 65 that feeds back 60 into an electronic controller 75.

The electronic controller 75 may act to control the operating parameters of the optical components. The electronic controller can be one or more of a microprocessor, field programmable gate array (FPGA), application specific integrated circuit (ASIC), operational amplifiers, comparators, or any other electrical components capable of providing control signals. One control signal 70 from electronic controller 75 may consist of parameters like the gain of an amplifier, which may be given as a voltage level or digitally encoded as a command sent to the amplifier module to control optical power emitted by the amplifier, for example, an erbium-doped fiber amplifier (EDFA). Another control signal 80 may be a timing signal in the form of a rising or falling edge of an electrical pulse sent to the optical pulse generator to control the timing and length of any optical pulses emitted by the pulse generator that may, for example, be in the form of a semiconductor optical amplifier (SOA).

Figure 2:
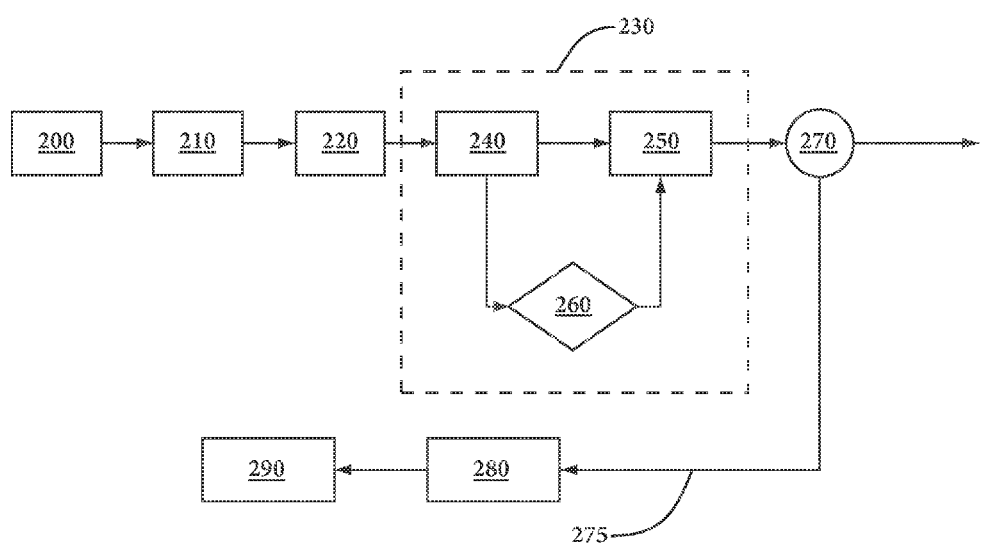
FIG. 2 illustrates a prior art optical electronic safety circuit.

The diagram of FIG. 2 provides an example of a prior art safety method used in fiber optic telecom systems. In this particular telecom system is shown a laser 200 feeding through a semiconductor optical amplifier (SOA) 210 and an erbium-doped fiber amplifier (EDFA) 220. In this approach an optical safety circuit 230 is inserted in the scheme before a circulator 270. Safety Circuit 230 uses a power meter 240 to monitor the energy level and via a control circuit 260 an optical switch or variable optical attenuator (VOA) 250 adjusts the power of the outgoing light. In this type of telecom system returned light 275 enters a receiver EDFA 280 and on to detector 290. As mentioned previously a disadvantage of such prior art optical safety circuit methods is that each component of the optical safety circuit is an active device with a possible failure mode. If any one of these three components were to fail to operate properly, the safety mechanism may fail to operate. The use of such systems requires testing and approval from a certification body, which can be a costly exercise.

Ideally, the power limiter will function to prevent the optical power leaving the enclosure from exceeding a threshold, but otherwise not interfere with the emitted light. Additionally, the ideal optical power limiter will be a passive device that limits the optical power automatically through an intrinsic physical property of the limiter. The ideal power limiter will provide a level of reliability and safety that otherwise would be cost prohibitive to achieve and validate using an actively controlled power limiting device. Finally, an ideal optical power limiter will be fully reversible, such that when the input power is reduced below the safety threshold, the optical power passes through the device undisturbed.

A well known non-linear scattering mechanism in fiber optic waveguides is called stimulated Brillouin scattering (SBS). In the SBS process, a pump wave generates acoustic waves through the process of electrostriction. The electrostriction causes a periodic modulation of the refractive index of the glass that creates an acoustic grating. The grating scatters the light in the reverse direction of propagation as a Raman Stokes wave. Eventually, as the optical power of the pump is increased, more of the pump power is scattered in the reverse direction until nearly all of the pump power is being scattered back toward the optical source. In the description to follow, we propose using the SBS process in a short (less than 1 km) coil of fiber that has been designed for a lower SBS threshold power than standard SMF28 fiber. This power limiting fiber and its placement in the overall scheme is illustrated in FIG. 3.

Figure 3:
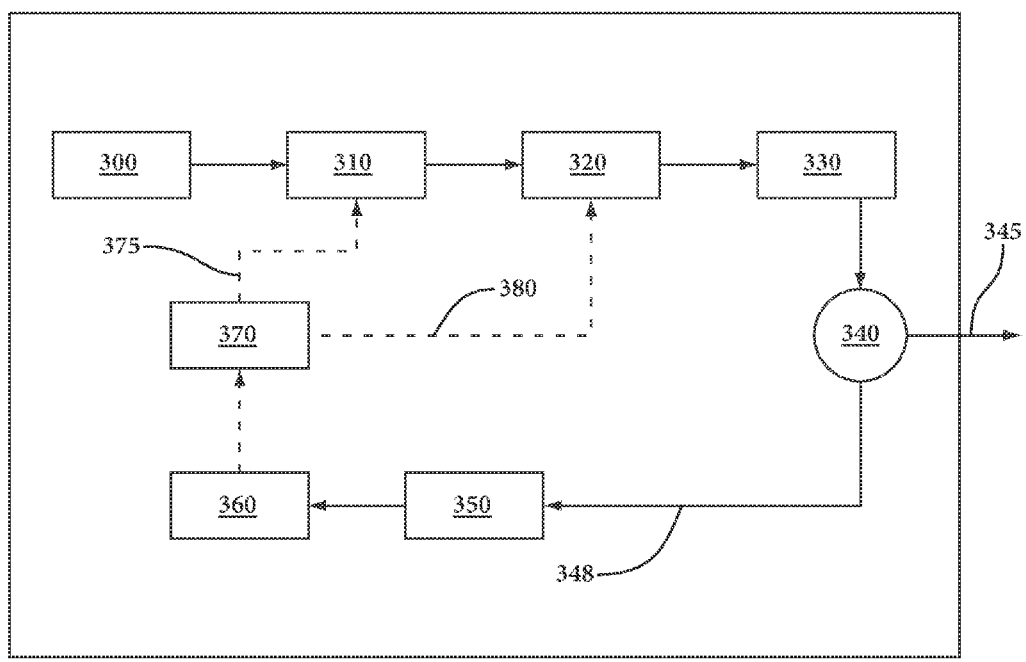
FIG. 3 illustrates a fiber optic sensor interrogator schematic with an inserted passive power limiting fiber to provide enhanced safety.

In FIG. 3 we see a high-level optical interrogator schematic similar to FIG. 1 in which the power limiting fiber coil is placed in the light-emitting path (upper path) after the optical pulse generator and before the circulator/coupler.

As described previously the light emitting path may consist of a laser 300, an optical amplifier 310, and an optical pulse generator 320, all located before passive optical power limiter 330. As mentioned previously, the light emitting path may also be a laser only in the case of continuous wave (CW) systems or naturally pulsed laser systems. The proposed passive optical power limiter device 330 is the coil of fiber discussed previously that has been designed for a lower SBS threshold power. The coil may have a fixed attenuation to the optical energy passing through it when the optical power level is below a threshold and have a larger attenuation when the optical energy passing through it is above a threshold. As the input power into the coil increases beyond the threshold level, the power that is transmitted through the coil will remain at or near the threshold level or fall off. The coil attenuation may be fully reversible when power levels return to below the threshold level. Additionally, and importantly, coil 330 will be located in the interrogator system such that it only affects the light emitted by the interrogator light from the light-emitting path, but has no effect on the sensor light that is returning to the interrogator and is directed to the light-receiving path. This is important because the sensing light returning to the interrogator is typically weaker than the transmitted light and may even be many orders of magnitude weaker than the transmitted light, and thus any additional attenuation will degrade the sensing signal. Additionally, any disturbance to the returned light through mechanisms like wavelength selective attenuation or other non-linear effects may negatively affect sensing parameters like accuracy, resolution, and repeatability.

Turning now to the light-receiving path (lower path) the returned back-scattered signals 348 from the region of interest 345 are fed to an optical receiver/detector 350 that may contain photo-detectors as well as hardware and/or software needed to detect and analyze the returned signals. The analog signals from receiver/detector 350 may then pass to an analog-to-digital (ADC) converter 360 that feeds back into an electronic controller 370.

The electronic controller 370 may act to control the operating parameters of the optical components. The electronic controller can be one or more of a microprocessor, field programmable gate array (FPGA), application specific integrated circuit (ASIC), operational amplifiers, comparators, or any other electrical components capable of providing control signals. One control signal 375 from electronic controller 370 may consist of parameters like the gain of an amplifier, which may be given as a voltage level or digitally encoded as a command sent to the amplifier module to control optical power emitted by the amplifier, for example, an erbium-doped fiber amplifier (EDFA). Another control signal 380 may be a timing signal in the form of a rising or falling edge of an electrical pulse sent to the optical pulse generator to control the timing and length of any optical pulses emitted by the pulse generator that may, for example, be in the form of a silicon-optical amplifier (SOA).

One method for designing a fiber with low SBS threshold is by using a single-mode fiber with high numerical aperture to produce a smaller mode-field diameter. Specialty fibers are available from major fiber vendors with reduced mode field, and thus also reduced SBS threshold. More exotic specialty fibers may be used for orders of magnitude reduction in SBS. For example, chalcogenide glass fibers as reported by Sanghera, et al. "Nonlinear Properties of chalcogencide glass fibers" [Journal of Optoelectronics and Advanced Materials, Vol 8, No. 6, December 2006, pg. 2148].

A desirable quality of the power limiting fiber is that its Brillouin scattering side-bands do not coincide with Brillouin side-bands of the sensing or transmitting fiber that may be connected externally, otherwise the Brillouin scattering energy produced in the power limiting device may effectively reduce the optical power capacity of the external fiber under normal operating power levels.

To validate the concept, an experiment was performed using high numerical aperture single-mode fiber made by OFS Specialty Fibers.

Figure 4:
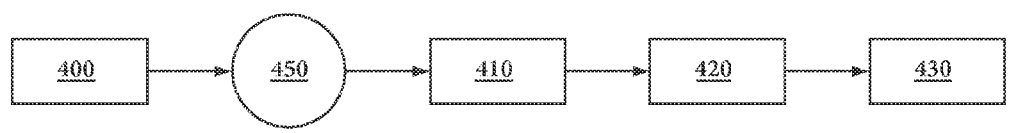
FIG. 4 illustrates the use of a baseline reference configuration to test the effect of power excursions in a fiber interrogator system.
Figure 5:
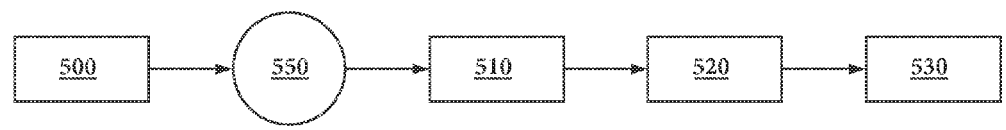
FIG. 5 illustrates the use of an added Brillouin Stimulation configuration to test the effect of power excursions in a fiber interrogator system.
Figure 6:
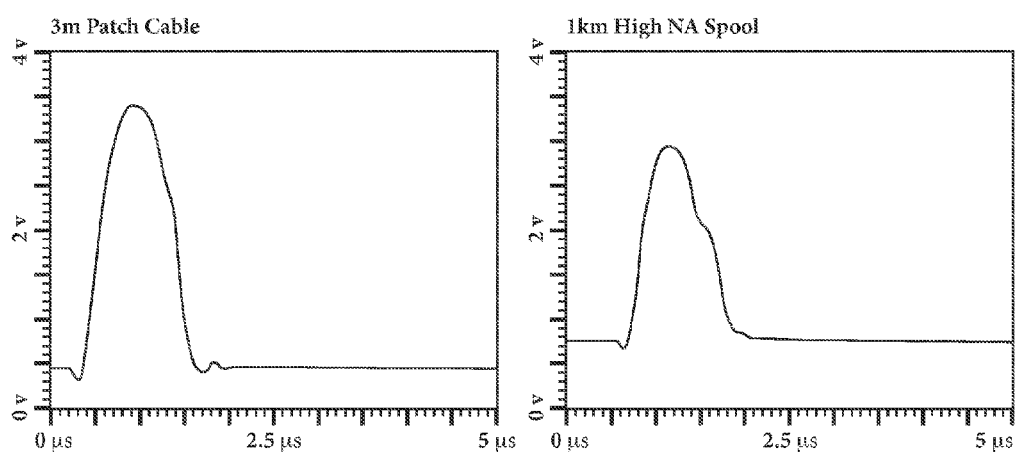
FIG. 6 illustrates the test results based on a side-by-side comparison of the power profile measured from a fiber optic interrogator system with and without an added passive power limiting fiber.
Figure 7:
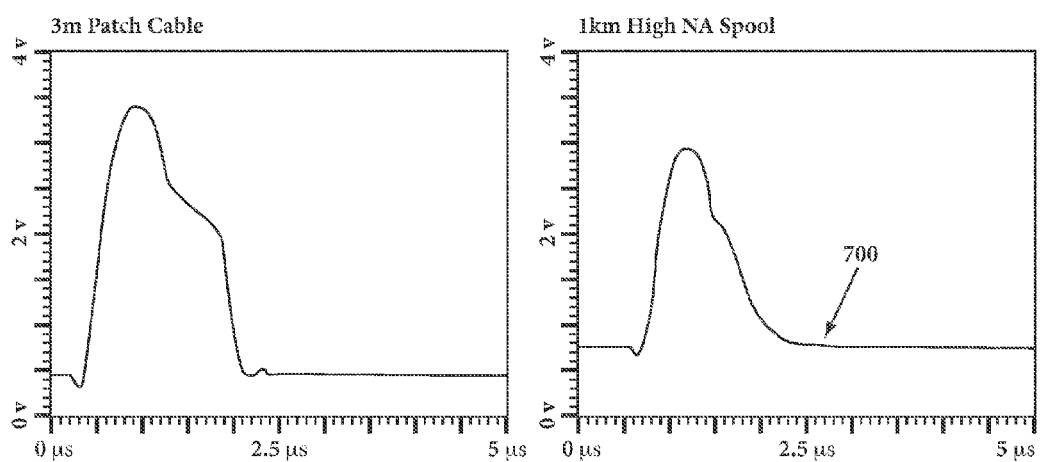
FIG. 7 illustrates the test results based on a side-by-side comparison of the power profile measured from a fiber optic interrogator system with and without an added passive power limiting fiber.
Figure 8:
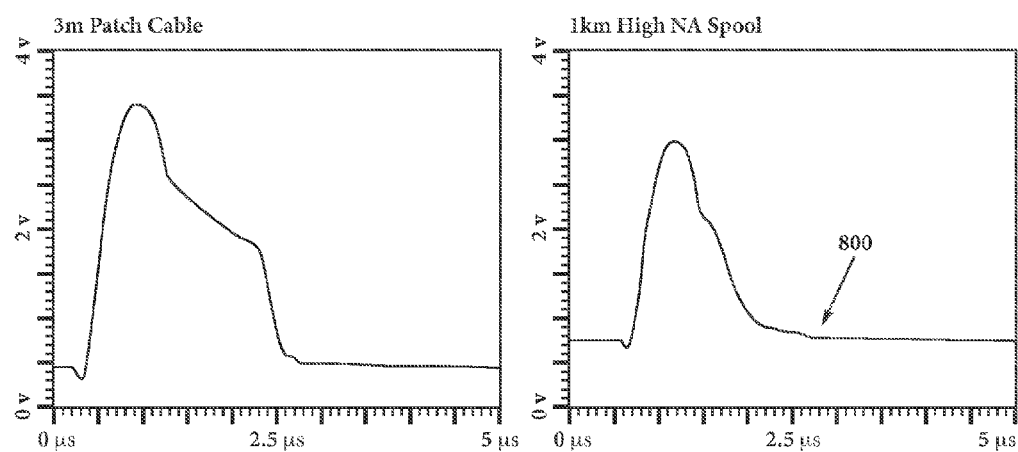
FIG. 8 illustrates the test results based on a side-by-side comparison of the power profile measured from a fiber optic interrogator system with and without an added passive power limiting fiber.
Figure 9:
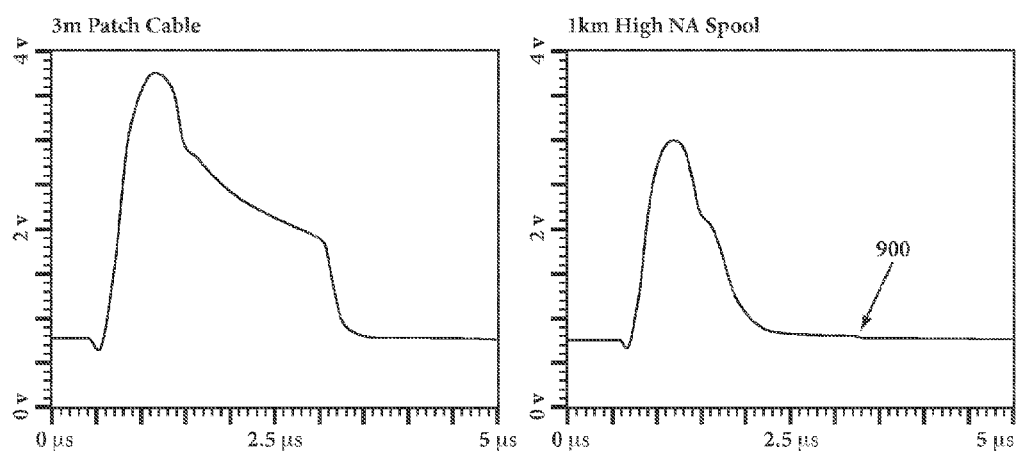
FIG. 9 illustrates the test results based on a side-by-side comparison of the power profile measured from a fiber optic interrogator system with and without an added passive power limiting fiber.
Figure 10:
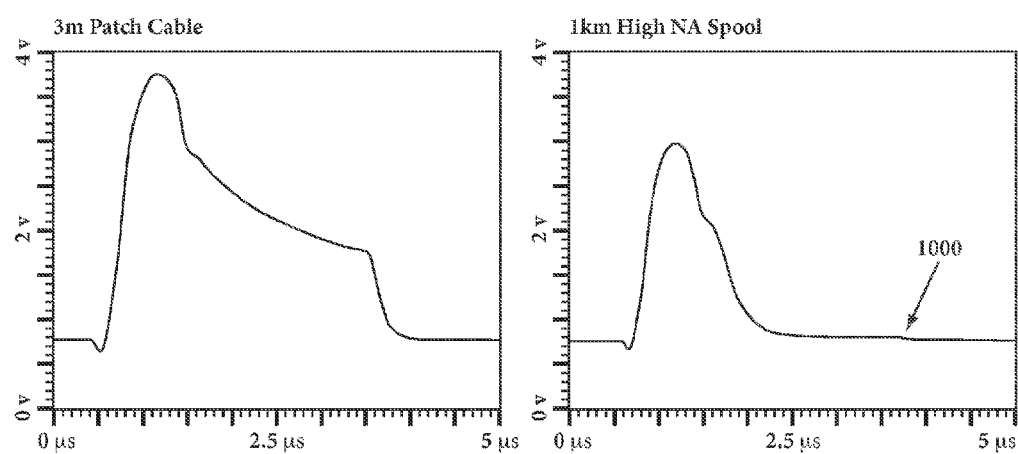
FIG. 10 illustrates the test results based on a side-by-side comparison of the power profile measured from a fiber optic interrogator system with and without an added passive power limiting fiber.
Figure 11:
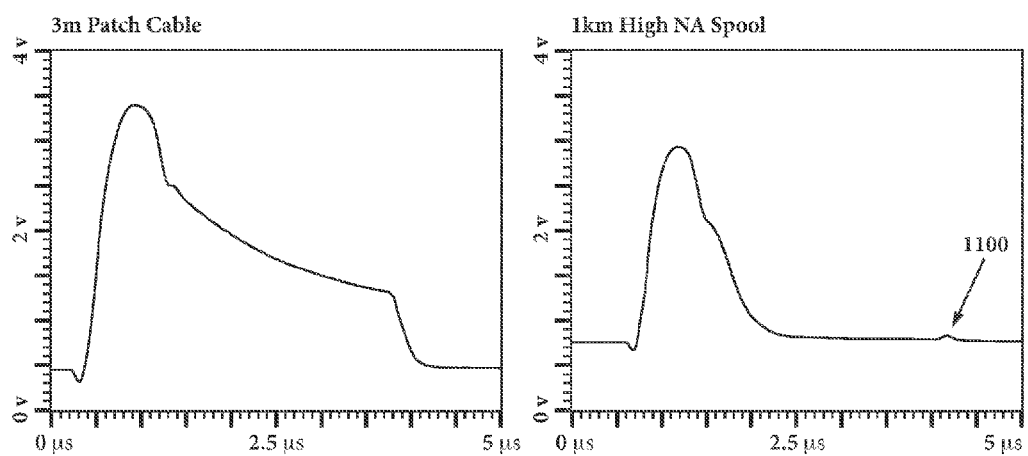
FIG. 11 illustrates the test results based on a side-by-side comparison of the power profile measured from a fiber optic interrogator system with and without an added passive power limiting fiber.
Figure 12:
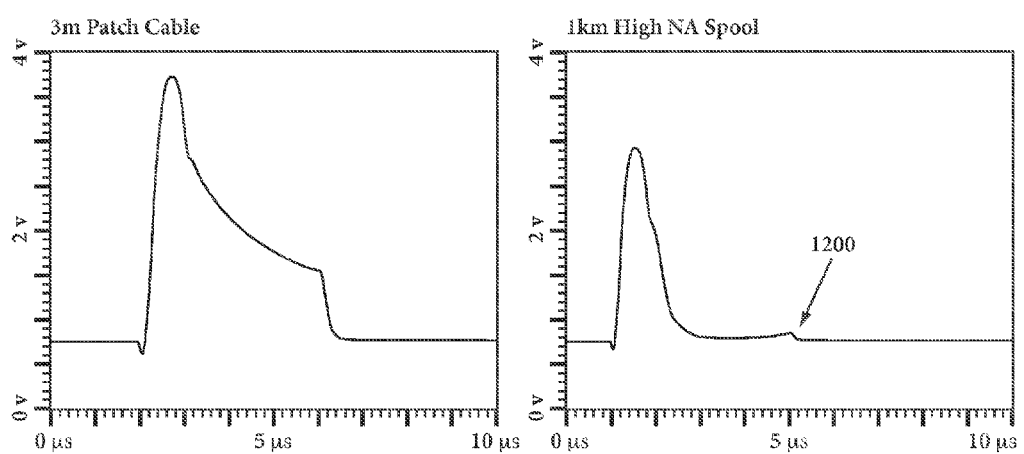
FIG. 12 illustrates the test results based on a side-by-side comparison of the power profile measured from a fiber optic interrogator system with and without an added passive power limiting fiber.
Figure 13:
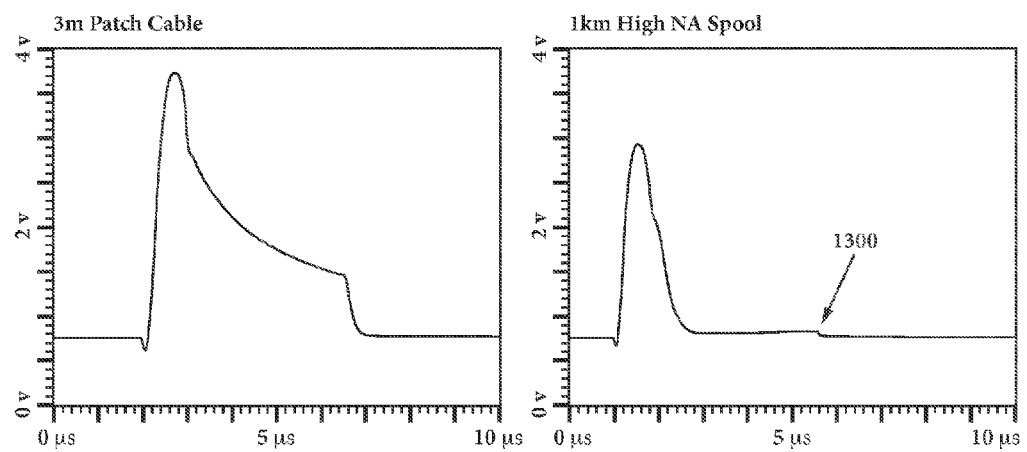
FIG. 13 illustrates the test results based on a side-by-side comparison of the power profile measured from a fiber optic interrogator system with and without an added passive power limiting fiber.
Figure 14:
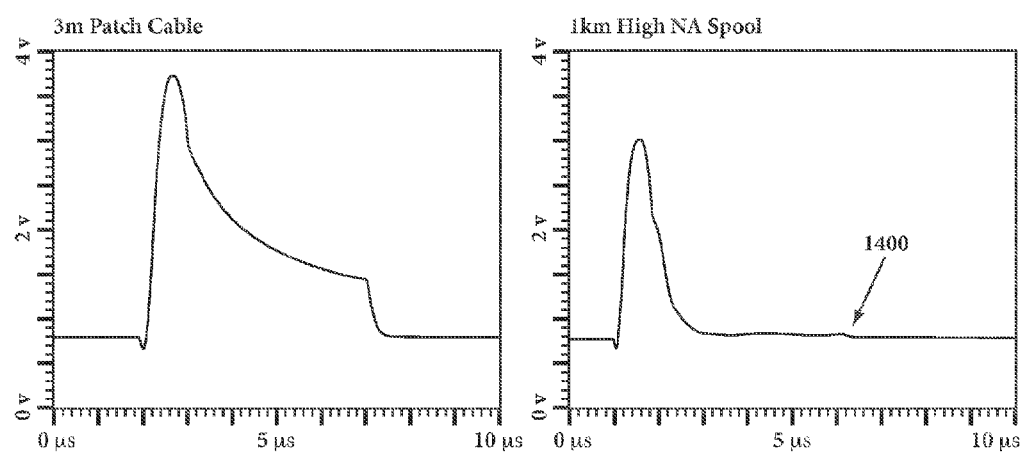
FIG. 14 illustrates the test results based on a side-by-side comparison of the power profile measured from a fiber optic interrogator system with and without an added passive power limiting fiber.
Figure 15:
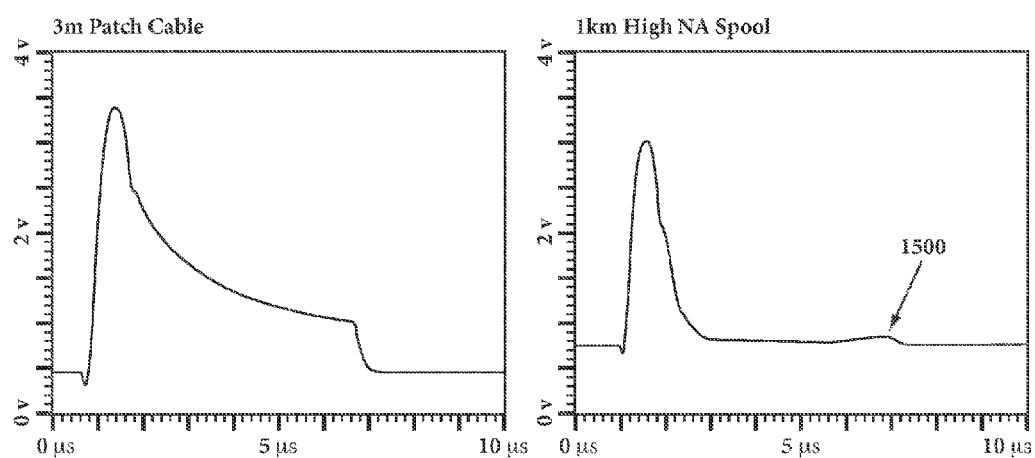
FIG. 15 illustrates the test results based on a side-by-side comparison of the power profile measured from a fiber optic interrogator system with and without an added passive power limiting fiber.

A test was performed to determine the viability of using the stimulated Brillouin scattering effect that is intrinsic to optical fiber to selectively attenuate pulses that exceed a safe average optical power level. To perform these tests, two optical configurations were used: a reference configuration containing a 3-meter patch cable, shown in FIG. 4 and the test configuration containing 1 Km of high-NA fiber with low SBS threshold, shown in FIG. 5. In FIG. 4 (the test configuration) a fiber interrogator 400 is fed through a 3 meter patch cable 450, then trough a variable optical attenuator 410 and an optical receiver module 420 with the results displayed on an oscilloscope 430. The test configuration is almost identical with the 3-meter patch cable now replaced by the high-NA fiber 550. The other elements—fiber interrogator 500, variable optical attenuator 510, optical receiver module 420, and oscilloscope 530, are identical with their counterparts 400, 410, 420, and 430 in FIG. 4.

For launching the optical pulses into the fiber, a fiber sensor interrogator was configured such that the receivers were disconnected inside the box to eliminate the chance of damage to the receivers due to strong reflections. The launch EDFA was set to its maximum gain setting level of 300 mA. To change the pulse power, the length of the pulse was increased, starting at 1000 ns, going up to 80 microseconds. The following FIGS. 6 through 15 show comparison results between the two configurations side by side using the same launch pulse power and width with the left side being configured with the 3-meter patch cable and the right side using the high-NA fiber spool.

In each of the figures is shown the test results on a Tectronix oscilloscope. The vertical (y-axis) scale is voltage marked off in major increments of 0.5 volts. The horizontal (x-axis) scale is time marked off in major increments of 500 nanoseconds for FIGS. 6-11 and 1000 nanoseconds for FIGS. 12-15. As the test proceeds from FIGS. 6 thru FIG. 15 it can be seen that the SBS in the high-NA fiber begins attenuating the pulse after its full-width half-max duration exceeds the maximum allowed width of 500 ns (results on right). On the left, where the 3-meter patch cable is used, the natural decay of the EDFA gain shows a gradual decline in power, but remains well above baseline for the entire pulse duration. However, after going through the high-NA fiber spool on the right, the pulse after 500 ns remains attenuated to near baseline even when its duration is increased to 6 microseconds.

Figure 16:
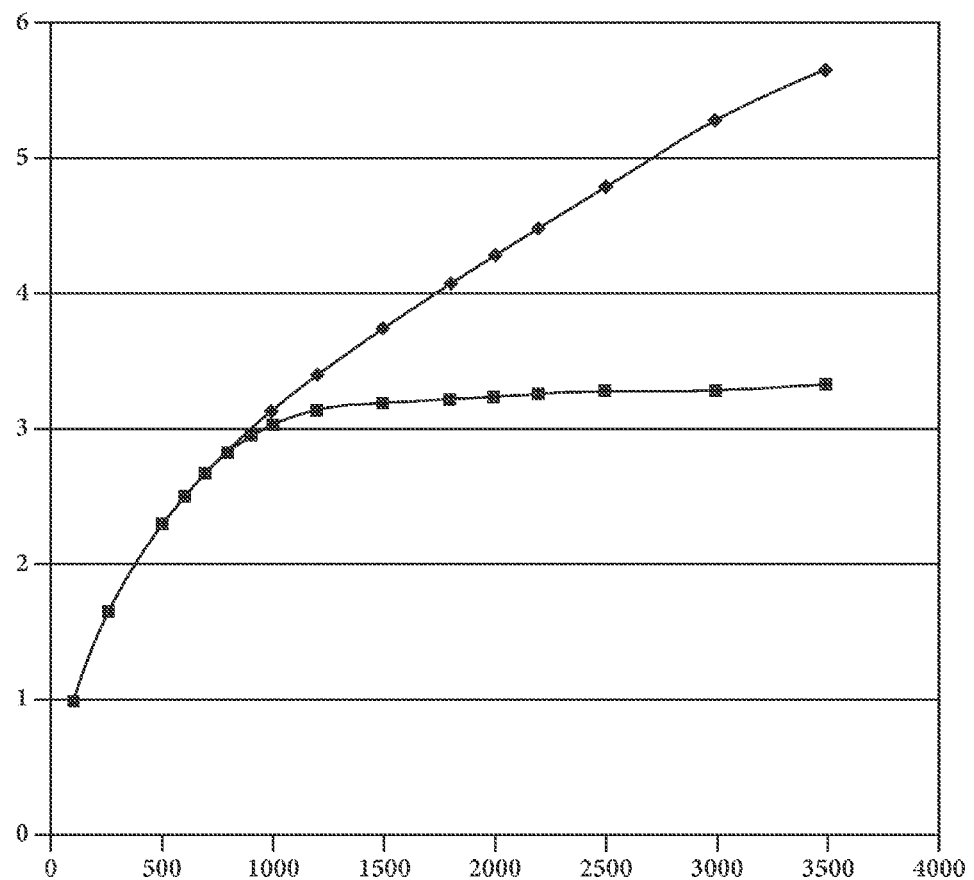
FIG. 16 illustrates the overall effect of power limitation of the passive power limiting fiber.

To further clarify these results FIG. 16 is a plot in which the same tests were performed as in FIGS. 6-15 but the Optiphase V-600 optical receiver (420, 520) is replaced by an EXFO FPM-600 optical power meter. The data from the optical power meter is shown in FIG. 16 with optical power in milliwatts on the vertical axis and pulse width in nanoseconds on the horizontal axis. The plot clearly shows that while the upper plot from the 3-meter patch cable configuration shows a near linear increase in power as the pulse width increases (slightly less than linear due to EDFA roll-off), however the lower plot shows that with the high-NA fiber acting as a power limiter, the optical power transmitted to the power meter increases in sync with the 3 m path cable configuration until about 3 mW, where it begins to asymptotically approach a power limit imposed by the power limiting fiber.

The results clearly show that the proper use of a high-NA fiber with low SBS threshold in a fiber provides an effective passive optic sensor interrogator. This approach is distinctive because it provides a passive, simple, and low-cost method of optical power limiting. Because this approach is passive and based on fundamental physical principles of glass waveguides, it provides a highly reliable, low-cost mechanism for optical power limiting. Whereas other methods, based on active devices and control circuits will require very costly testing and certification before being approved for use with fiber interrogators in hazardous areas.

Although certain embodiments and their advantages have been described herein in detail, it should be understood that various changes, substitutions and alterations could be made without departing from the coverage as defined by the appended claims. Moreover, the potential applications of the disclosed techniques is not intended to be limited to the particular embodiments of the processes, machines, manufactures, means, methods and steps described herein. As a person of ordinary skill in the art will readily appreciate from this disclosure, other processes, machines, manufactures, means, methods, or steps, presently existing or later to be developed that perform substantially the same function or achieve substantially the same result as the corresponding embodiments described herein may be utilized. Accordingly, the appended claims are intended to include within their scope such processes, machines, manufactures, means, methods or steps.

What is claimed:

1. In a fiber optic sensor interrogation systems that includes at least a light emitting path for sending interrogation light signals and a light receiving path for receiving returned light signals, a method for enhancing safety by:
   a. sending the interrogation light signals from the light emitting path through a circulator/coupler device out into a region of interest to be measured;
   b. returning backscattered light from the region of interest through the circulator/coupler device into the light receiving path; and
   c. placing a passive power limiting fiber with a low stimulated Brillouin scattering threshold in the light emitting path before the circulator/coupler device.

2. The method for enhancing safety of claim 1 wherein the returning of backscattered light from the region of interest through the circulator/coupler into the light receiving path further includes at least;
   a. feeding the backscattered light into an optical receiver/detector to detect and analyze the returned signals.

3. The method for enhancing safety of claim 1 wherein the passive power limiting fiber with a low stimulated Brillouin scattering threshold is a single-mode fiber with high numerical aperture to produce a smaller mode-field diameter.

4. The method for enhancing safety of claim 1 wherein the passive power limiting fiber with a low stimulated Brillouin scattering threshold is a chalcogencide glass fiber.

5. The method for enhancing safety of claim 1 wherein the sending of the interrogation light signals includes at least;
   a. providing a light signal;
   b. providing optical amplification to that light signal.

6. The method for enhancing safety of claim 5 wherein the sending of the interrogation light signals further comprises;
   a. providing pulse generation to that light signal.

7. The method for enhancing safety of claim 6 wherein the returning of backscattered light from the region of interest through the circulator/coupler into the light receiving path further includes at least;
   a. feeding the backscattered light into an optical receiver/detector to detect and analyze the returned signals.

8. The method for enhancing safety of claim 7 wherein the passive power limiting fiber with a low stimulated Brillouin scattering threshold is a single-mode fiber with high numerical aperture to produce a smaller mode-field diameter.

9. The method for enhancing safety of claim 7 wherein the passive power limiting fiber with a low stimulated Brillouin scattering threshold is a chalcogencide glass fiber.

10. A fiber optic sensor interrogation system with inbuilt passive power limiting capability comprising:
    a. a light source;
    b. optical amplification circuitry acting on that light source;
    c. pulse generation circuitry acting on that amplified light source;
    d. wherein the light source, optical amplification circuitry and pulse generation circuitry represent a light emitting path for the fiber optic interrogation system;
    e. a circulator/coupler device that directs light from the light emitting path for the fiber optic interrogation system into a region of interest for sensing, and receives and redirects backscattered light from the region of interest;

f. a passive power limiting fiber with a low stimulated Brillouin scattering threshold placed in the light emitting path before the circulator/coupler device.

11. The fiber optic sensor interrogation system with inbuilt passive power limiting capability of claim 10 further comprising:
   a. an optical receiver/detector that receives the redirected backscattered light from the region of interest.

12. The fiber optic sensor interrogation system with inbuilt passive power limiting capability of claim 11 further comprising:
   a. an electronic control system for providing control parameters to the optical amplification circuitry acting on the light source and the pulse generation circuitry acting on the light source.

13. The fiber optic sensor interrogation system with inbuilt passive power limiting capability of claim 12 wherein the passive power limiting fiber with a low stimulated Brillouin scattering threshold is a single-mode fiber with high numerical aperture to produce a smaller mode-field diameter.

14. The fiber optic sensor interrogation system with inbuilt passive power limiting capability of claim 12 wherein the passive power limiting fiber with a low stimulated Brillouin scattering threshold is a chalcogencide glass fiber.

15. The fiber optic sensor interrogation system with inbuilt passive power limiting capability of claim 10 wherein the laser, optical amplification circuitry and pulse generation circuitry are combined into a single component.

16. The fiber optic sensor interrogation system with inbuilt passive power limiting capability of claim 15 further comprising:
   a. an optical receiver/detector that receives the redirected backscattered light from the region of interest.

17. The fiber optic sensor interrogation system with inbuilt passive power limiting capability of claim 16 wherein the passive power limiting fiber with a low stimulated Brillouin scattering threshold is a single-mode fiber with high numerical aperture to produce a smaller mode-field diameter.

18. The fiber optic sensor interrogation system with inbuilt passive power limiting capability of claim 16 wherein the a passive power limiting fiber with a low stimulated Brillouin scattering threshold is a chalcogencide glass fiber.

19. A fiber optic sensor interrogation system with inbuilt passive power limiting capability comprising:
   a. a light source having a light emitting path;
   b. a circulator/coupler device that directs light from the light emitting path for the fiber optic interrogation system into a region of interest for sensing, and receives and redirects backscattered light from the region of interest;
   c. a passive power limiting fiber with a low stimulated Brillouin scattering threshold placed in the light emitting path before the circulator/coupler device.

20. The fiber optic sensor interrogation system with inbuilt passive power limiting capability of claim 19 further comprising:
   a. an optical receiver/detector that receives the redirected backscattered light from the region of interest.

21. The fiber optic sensor interrogation system with inbuilt passive power limiting capability of claim 19 wherein the passive power limiting fiber with a low stimulated Brillouin scattering threshold is a single-mode fiber with high numerical aperture to produce a smaller mode-field diameter.

22. The fiber optic sensor interrogation system with inbuilt passive power limiting capability of claim 19 wherein the passive power limiting fiber with a low stimulated Brillouin scattering threshold is a chalocogencide glass fiber.

* * * * *